(12) United States Patent
Bases

(10) Patent No.: US 6,391,911 B1
(45) Date of Patent: May 21, 2002

(54) COADMINISTRATION OF LUCANTHONE AND RADIATION FOR TREATMENT OF CANCER

(76) Inventor: Robert E. Bases, 1 Mohegan Pl., New Rochelle, NY (US) 10804

( * ) Notice: Subject to any disclaimer, the term of this patent is extended or adjusted under 35 U.S.C. 154(b) by 0 days.

(21) Appl. No.: 09/289,326

(22) Filed: Apr. 9, 1999

Related U.S. Application Data

(60) Provisional application No. 60/121,941, filed on Feb. 26, 1999.

(51) Int. Cl.[7] ............................................... A61K 31/38
(52) U.S. Cl. ....................................... 514/437
(58) Field of Search .......................... 514/437

(56) References Cited

U.S. PATENT DOCUMENTS 5,580,998 A * 12/1996 Bouchard et al. ........... 514/510

OTHER PUBLICATIONS

M.D. Walker, "Randomized Comparisions of Radiotherapy and Nitrosoureas for the Treatment of Malignant Giloma After Surgery", N. Eng. J. Med., 303: 1323–1329 (1980).
R.E. Bases et al., "Topoisomerase Inhibition by Lucanthone, an Adjuvant in Radiation Therapy", Int. J. Radiat. Oncol. Biol. Phys., 37: 1133–1137 (1997).
S. Turner et al., "The Adjuvant Effect of Lucanthone (Miracil D) in Clinical Radiation Therapy", Radiology, 114: 729–731 (1975).
Corbett et al., Antitumor activity of N–[[1–[[2–(diethylamino)ethyl]amino]–9–oxo–9H–thioxanthen–4–yl]methyl] methanesulfonamide (WIN33377) and analogues, Exp. Opin. Invest Drugs (1994) 3(12):1281–1292.
Del Rowe, et al. Accelerated Regression of Brain Metastases in Patients Receiving Whole Brain Radiation and the Topoisomerase II Inhibitor, Lucanthone, Clinical Investigation, 1998, pp. 1–5.
Wentland, et al., Anti–Solid Tumor Efficacy and Preparation of N–[[1–[[2–(Diethyamino)Ethyl]Amino]–9–Oxi–9H–Thioxanthen–4–YL]Methyl]Methanesulfonamide (Win 33377) and Related Derivatives, Bioorganic & Medicinal Chemistry Letters, vol. 4, No. 4, pp. 609–614, 1994.

* cited by examiner

Primary Examiner—Jerome D. Goldberg
(74) Attorney, Agent, or Firm—Kenyon & Kenyon

(57) ABSTRACT

Disclosed is a method of treating a cancer of the central nervous system in a host including administering radiation to the host; and administering lucanthone to the host; wherein the radiation and lucanthone are administered in amounts effective to cause the arrest or regression of the cancer of the central nervous system in the host. Also disclosed is method of treating tumors of the central nervous system including inducing base damage to a tumor cell's DNA; and inhibiting excision repair of that damage by providing lucanthone to the cell.

30 Claims, No Drawings

COADMINISTRATION OF LUCANTHONE AND RADIATION FOR TREATMENT OF CANCER

Cross References to Related Applications:

This application claims the benefit of priority to U.S. patent application Ser. No. 60/121,941 filed Feb. 26, 1999.

BACKGROUND OF THE INVENTION

1. Field of the Invention

In an aspect, the invention relates to treatment of cancer, more particularly to coadministration of lucanthone and radiation for treatment of cancer.

2. Description of the Related Art

Management of patients with central nervous system (CNS) cancers remains a formidable task. Conventional chemotherapy administered systemically as a monotherapy tends not to be very effective because conventional chemotherapeutic agents tend not to reach portions of the CNS in effective amounts, primarily because of the blood-brain barrier. For example, etoposide and actinomycin D, two commonly used oncology agents that inhibit topoisomerase II, fail to cross the blood-brain barrier in useful amounts. Radiation therapy improves median survival. P. L. Kornblith et al, Chemotherapy for Malignant Gliomas, J. Neurosurg. 68: 1–17 (1988). This document, and all others cited to in this patent, is incorporated by reference as if reproduced fully herein. The benefit of radiotherapy, however, is limited by several factors. Although intrinsic radioresistance and rapid cellular proliferation may contribute to therapeutic inefficacy, dose escalation has not yet yielded superior results and is limited by the radiation tolerance of normal brain as reported by O. M. Solazar et al., *High Dose Radiation Therapy in the Treatment of Malignant Gliomas: Final Report*, Int. J. Radial. Oncol. Biol. Phys., 3: 1733–1740 (1979).

Combinations of chemotherapy and radiation have been experimented with in the treatment of CNS cancers. The additional use of nitrosoureas adds a modest gain for selected patients. M. D. Walker, *Randomized Comparisons of Radiotherapy and Nitrosoureas for the Treatment of Malignant Glioma After Surgery*, N. Eng. J. Med., 303: 1323–1329 (1980). U.S. Pat. No. 5,637,085 to Cardinale, with an issue date of Jun. 10, 1997, discloses a method and composition for intralesional therapy of solid cancer tumors, and especially brain tumors, comprising delivering a compound of a 1,2,4-benzotriazine oxide contained in a biodegradable, slow release polymer and subjecting the cancer tumors to irradiation therapy.

A problem with combining chemotherapy and radiation is that the blood-brain barrier interferes with transport of the chemotherapeutic agent into areas of the CNS, just as in monotherapy using chemotherapeutic agents. This reduces effectiveness of such therapies. For instance, compounds such as etoposide may be included in many multidrug protocols in medical oncology. However, etoposide crosses the blood-brain barrier poorly, thereby restricting its use in patients with central nervous system (CNS) lesions. The rapid induction of secondary leukemia in 1%-5% of patients is an obvious disadvantage of etoposide. Despite development of a number of different protocols, the overall survival of patients with CNS lesions such as glioblastoma multiforme, treated with surgery, radiation and chemotherapy, remains a dismal ten per cent.

There is therefore a need for a combination of chemotherapeutic agents and radiation that addresses the problems noted above.

SUMMARY OF THE INVENTION

In an aspect, the invention relates to a method of treating a cancer of the central nervous system in a host comprising administering radiation to the host, and administering lucanthone to the host; wherein the radiation and lucanthone are administered in amounts effective to cause the arrest or regression of the cancer of the central nervous system in the host. In another aspect, the invention relates to a method of treating tumors of the central nervous system comprising inducing base damage to a tumor cell's DNA, and inhibiting excision repair of that damage by providing lucanthone to the cell.

DETAILED DESCRIPTION OF THE INVENTION

The inventor has unexpectedly discovered that lucanthone may be advantageously administered, together with administration of radiation, in the treatment of cancers of the central nervous system, wherein the radiation and lucanthone are administered in amounts effective to cause the arrest or regression of the cancer of the central nervous system in the host.

Part of lucanthone's particular advantage in treating central nervous system cancers is that the inventor has established lucanthone's surprising ability to cross the blood-brain barrier in test animals, such as mice and rats. The inventor also has inferred its surprising ability to cross the barrier in humans. Therefore, lucanthone may be administered in physiologically tolerable amounts so as to have activity in the central nervous system, whereas other chemotherapeutic or radiosensitizing agents may not be so administered.

Lucanthone is a chemotherapeutic or radiosensitizing intercalating agent. For convenience, the term lucanthone is taken to include lucanthone proper, as 1-diethylaminoethylamino-4-methyl-10-thiaxanthenone, together with physiologically tolerated derivatives, analogs, and salts thereof. Such physiologically tolerated derivatives, analogs, and salts include, but are not limited to, Hycanthone, indazole analogues of lucanthone, and other analogs such as those disclosed in Thomas Corbett et al., Antitumor Activity of N-[[1-[[2-(diethylamino)ethyl]amino]-9-oxo-9H-thiaxanthen-4-yl]methyl]methanesulfonamide (WIN33377) and analogues, Exp. Opin. Invest. Drugs 3:1281–1292 (1994); and Mark P. Wentland et al., Anti-solid Tumor Efficacy and Preparation of N-[[1-[[2-(diethylamino)ethyl]amino]-9-oxo-9H-thiaxanthen-4-yl]methyl]methanesulfonamide (WIN33377) and Related Derivatives, Bioorg. & Med. Chem Lett. 4:609–614 (1994).

Lucanthone, which has been marketed as Nilodin or Miracil D, has been used as a treatment for schistomiasis. Lucanthone has been known to have an cytotoxic or cytostatic effect on growing cells. The enhanced joint lethal action of lucanthone and ionizing radiation in cells may be accounted for by the production of DNA double strand breaks (DSB) in cleavable complexes because of lucanthone's inhibition of topoisomerase II, combined with the DSB induced by radiation alone. R. Bases, DNA Intercalating Agents as Adjuvants in Radiation Therapy, *Int J Radiat Oncol Biol Phys* 4:345–346 (1978) (editorial); R. E. Bases et al., Topoisomerase Inhibition by Lucanthone, an Adjuvant in Radiation Therapy, *Int J Radiat Oncol Biol Phys* 37:1133–1137 (1997).

Topoisomerase II may also be implicated in the mechanism of radiation induced DSB by an additional mechanism.

When DNA bases are damaged by ionizing radiation, they are first removed by cells' base excision repair enzymes, which first remove the damaged bases (by a glycosylase) and leave abasic sites. Removal of abasic sites is achieved in the second step, performed by endonucleases that cause strand scission and leave 3' OH groups, which are required acceptors in DNA repair synthesis. Subsequent steps include removal of 5' phosphate groups at the sites of excised bases, followed by gap filling by DNA polymerase β, which inserts appropriate replacement nucleotides. DNA ligase completes repair by sealing in the replacement nucleotides.

If the abasic sites are not removed they could continue to act as endogenous topoisomerase II poisons, thereby promoting (lethal) DSB. P. S. Kingma et al., Abasic Sites Stimulate Double-stranded DNA Cleavage Mediated by Topoisomerase II: DNA Lesions as Endogenous Topoisomerase II Poisons. *J Biol Chem* 270:21441–21444 (1995).

It seems likely that topoisomerase II inhibitors, like lucanthone and Actinomycin D, which induce DNA double strand breaks by inhibiting topoisomerase II, might also enhance DNA double strand breaks in cell DNA by interfering with the removal of abasic sites in the second step of base excision repair described above. If so, the endogenous abasic site topoisomerase II poisons would persist in the DNA, leaving them in place to cause more double strand breaks over a longer time, thereby leading to a more than additive lethal effect. Unpublished data of the inventor suggests that lucanthone inhibits purified uracil DNA glycosylase and human apurinic apyrimidinic endonucleases at serum concentrations that would be readily achievable by oral dosing. Thus, lucanthone may be able to inhibit the crucial first two steps of post-radiation repair.

Previous results showed that lucanthone inhibited postradiation repair by enhancing potentially lethal and sublethal damage in Hela cells and in Chinese hamster cells. R. Bases, Enhancement of X-ray Damage in HeLa Cells by Exposure to Lucanthone (Miracil D) Following Radiation, *Cancer Res* 30:2007–2011 (1970); D. B. Leeper et al., The Effect of Lucanthone (Miracil D) on Sublethal Radiation Damage in Chinese Hamster Cells, *Int J Radiat Oncol Biol Phys* 4:219–227 (1978). In fact, in irradiated HeLa cells, lucanthone immediately induced a more than additive cell lethal effect, but when lucanthone was added to cultures several hours after radiation it could no longer enhance lethality beyond the simple addition of joint effects. Presumably, after several hours of culture, potentially lethal damage had already been repaired.

Furthermore, in patients with oropharyngeal cancer and metastatic lung lesions, radiation-induced tumor regression was significantly accelerated when patients received 10 mg/Kg lucanthone concurrent with radiation therapy. S. Turner et al., The Adjuvant Effect of Lucanthone (Miracil D) in Clinical Radiation Therapy, *Radiology* 114:729–731 (1975). Similar results were obtained with the joint treatment of patients with cervical cancer. M. P. Nobler et al., Lucanthone as a Radiosensitizing Agent in the Treatment of Carcinoma of the Cervix, *Int J Radiat Oncol Biol Phys* 4:1039–1044 (1978).

An advantage of lucanthone is that DNA replication requires topoisomerase II activity, thereby creating selective toxicity for cycling cells, such as cancerous cells. Normal brain cells, most of which do not cycle, would be therefore less sensitive to lucanthone-based therapy, and would be less likely to be non-selectively damaged. Furthermore, lucanthone's effects on bone marrow and the gut are moderate and reasonably quickly reversible. Therefore, further chemotherapy and radiation after lucanthone therapy are not preempted due to chemotoxicity.

Lucanthone may be administered in a variety of routes, including orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In a preferable embodiment, lucanthone is administered orally.

Lucanthone may be administered in an amount effective to cause arrest or regression of the cancer of the central nervous system in a host, when radiation is also administered to the host. More preferably, lucanthone may be administered in an amount effective to achieve a serum level of at least about 2.0 micrograms/milliliter, still more preferably at least about 3.0 micrograms/milliliter. When administering lucanthone orally, a preferable dosage is at least about 5 mg/Kg/day, more preferably at least about 10 mg/Kg/day. Oral doses of lucanthone may be administered once or more than once per day. If oral doses are administered more than once per day, a preferable number of doses is three doses per day. If administering lucanthone intravenously, a preferable dosage is 10 mg/kg continuously. Another preferable intravenous dosage is 3.3 mg/kg three times per day for a non-continuous (i.e. limited) period, such as two hours. Lucanthone may be administered intravenously using a conventional non-saline infusion fluid, such as 5% dextrose in water. Lucanthone dosing schedules may be for a variety of time periods, for example up to six weeks, or as determined by one of ordinary skill.

Lucanthone may be (co)administered in the practice of this invention together with other chemotherapeutic agents or other pharmaceuticals. (Co)administration in the context of this invention is defined to mean the administration of more than one therapeutic benefit in the case of a coordinated treatment to achieve an improved clinical outcome. Continuing, certain agents are believed to increase permeability through the blood-brain barrier. K. Matsukado et al., Intracarotid Low Dose Infusion Selectively Increases Tumor Permeability Through Activation of Bradykinin B2 Receptors on Malignant Gliomas, Brain Research 792:10–15 (1998). Such agents may be (co)administered with pharmaceuticals and lucanthone to increase the concentration of the pharmaceuticals in CNS tumor lesions. This may enhance the effect seen with administration of lucanthone and radiation.

Radiation may be administered in a variety of fashions. For example, radiation may be electromagnetic or particulate in nature. Electromagnetic radiation useful in the practice of this invention includes, but is not limited to, x-rays and gamma rays. In a preferable embodiment, supervoltage x-rays (x-rays>=4 MeV) may be used in the practice of this invention. Particulate radiation useful in the practice of this invention includes, but is not limited to, electron beams, protons beams, neutron beams, alpha particles, and negative pi mesons. The radiation may be delivered using conventional radiological treatment apparatus and methods, and by intraoperative and stereotactic methods. Additional discussion regarding radiation treatments suitable for use in the practice of this invention may be found throughout Steven A. Leibel et al., *Textbook of Radiation Oncology* (1998) (publ. W. B. Saunders Company), and particularly in Chapters 13 and 14. Radiation may also be delivered by other methods such as targeted delivery, for example by radioactive "seeds," or by systemic delivery of targeted radioactive conjugates. J. Padawer et al., Combined Treatment with Radioestradiol lucanthone in Mouse C3HBA Mammary Adenocarcinoma and with Estradiol lucanthone in an Estrogen Bioassay, *Int. J. Radiat. Oncol. Biol. Phys.* 7:347–357 (1981). Other radiation delivery methods may be used in the practice of this invention.

The amount of radiation delivered to the desired treatment volume may be variable. In a preferable embodiment, radiation may be administered in amount effective to cause the arrest or regression of the cancer of a central nervous system in a host, when the radiation is administered with lucanthone. In a more preferable embodiment, radiation is administered in at least about 1 Gray (Gy) fractions at least once every other day to a treatment volume, still more preferably radiation is administered in at least about 2 Gray (Gy) fractions at least once per day to a treatment volume, even more preferably radiation is administered in at least about 2 Gray (Gy) fractions at least once per day to a treatment volume for five consecutive days per week. In a more preferable embodiment, radiation is administered in 3 Gy fractions every other day, three times per week to a treatment volume. In another more preferable embodiment, the first 23 fractions are administered to an initial treatment volume, while another 7 treatment fractions are delivered to a boost treatment volume. In yet another more preferable embodiment, a total of at least about 20 Gy, still more preferably at least about 30 Gy, most preferably at least about 60 Gy of radiation is administered to a host in need thereof. In another more preferable embodiment, radiation is administered to the whole brain, rather than to a treatment volume. When irradiating the whole brain, a maximum dosage of 30 Gy is recommended. In a most preferable embodiment, radiation is administered to the whole brain of a host, wherein the host is being treated for metastatic cancer.

In a preferable embodiment, the treatment volume comprises a contrast-enhancing lesion on a CT or MRI scan, more preferably a contrast-enhancing lesion and surrounding edema, still more preferably a contrast-enhancing lesion and surrounding edema on a CT or MRI scan plus at least about a 1 cm margin. In another preferable embodiment, the treatment volume comprises a contrast-enhancing lesion on a CT or MRI scan, still more preferably a contrast-enhancing lesion plus at least about a 1 cm margin, even more preferably a contrast-enhancing lesion plus at least about a 2.5 cm margin.

Treatment plans may include, but are not limited to, opposed lateral fields, a wedge pair of fields, rotation or multiple field techniques. CT-guided treatment planning is suggested to improve accuracy in the selection of field arrangements. Isodose distributions for the initial treatment volume and the cone-down treatment volume are suggested for all patients, including those with parallel opposed fields. Composite plans showing dose distribution to the initial treatment volume and the boost treatment volume are desirable. The minimum and maximum dose to the treatment volume are preferably kept to within about 10% of the dose at the center of the treatment volume.

A broad range of CNS cancers may be treated using the present invention. These cancers comprise both primary and metastatic cancers. In a preferable embodiment, lucanthone and radiation may be administered to patients suffering from primary brain tumors. Primary brain tumors treatable using the present invention include, but are not limited to glioblastoma multiforme, astrocytomas, medulloblastomas, acoustic neuromas, and tumors of the anterior and posterior pituitary. Cancers that have metastasized to the brain may also be treated using this invention. Such cancers include, but are not limited to, adenocarcinomas of the lung, squamous cell carcinomas of the lung, mammary adenocarcinomas, lymphomas, and leukemias.

It will be apparent to those skilled in the art that various modifications and variations can be made in the methods of the present invention without departing from the spirit or scope of the invention. Thus, it is intended that the present invention cover the modifications and variations of this invention provided they come within the scope of the appended claims and their equivalents. Additionally, the following examples are appended for the purpose of illustrating the claimed invention, and should not be construed so as to limit the scope of the claimed invention.

EXAMPLES

Example 1

Mouse Models

Ten six-week-old 18–20 gram female C3H-HeHa mice obtained from West Seneca Laboratories (West Seneca, N.Y.) were injected subcutaneously in the right nipple line with $1.4 \times 10^6$ viable C3H-BA mammary adenocarcinoma cells. With such inocula, 1–2-mm tumors were detectable within 3 days. If allowed to grow, they killed the mice in 36–38 days. This highly invasive tumor could grow rapidly from inocula as low as $10^4$ cells.

In order to minimize the influence of tumor size on drug distribution, drug was administered at various times during the course of tumor growth. Each day, from the seventh to eleventh day after injection, two mice were injected intraperitoneally with 1.27 mg $^3$H lucanthone methanesulfonate. Lucanthone methanesulfonate, after being labeled by tritium exchange of hydrogen, was 96%-99% pure by thin layer chromatography. Before injection in mice, the specific radioactivity of $^3$H lucanthone, originally 135 MBq/mg, was reduced to 67.5 MBq/mg by dilution with unlabeled lucanthone methanesulfonate. The total dose of radioactivity was 8.74 MBq (236 $\mu$Ci) in 0.44 ml. All mice were sacrificed on the twelfth day, at which time the tumors were all approximately the same size, 7–12 mm in greatest diameter.

Distribution of tritium-labeled material in tissues represents lucanthone and its metabolites. Following sacrifice by cervical dislocation, the wet weight of samples of various organ or tumor tissue was determined immediately. Samples (about 50 mg each) were placed in glass scintillation vials with metal foil-lined caps. An alkaline tissue solubilizer, Protosol (DuPont—NEN), was added for digestion; radioactivity was determined by liquid scintillation techniques, as recommended by the manufacturer. Quench corrections were made for each sample to avoid interference from colored substances in individual samples. Hair was shaved from the skin samples to avoid its contribution to the weight of the sample.

Enrichment of the $^3$H label was detected in tumor tissue relative to skin and muscle on the first and second days following drug injection. By contrast, in livers and kidneys, which are the principal excretory organs for this drug, higher concentrations were found than in the tumor. Brain, lung, and spleen showed little difference in $^3$H lucanthone uptake and removal. The time course of uptake and removal for the heart was similar to that of brain and muscle. The data indicated that lucanthone crossed the blood-brain barrier since the kinetics for the brain were indistinguishable from kinetics in organs, which lack special barriers.

Example 2

Radiolabeled Rat Models

Rats were injected with $^{125}$I-labeled lucanthone and $^{99m}$Tc-pertechnetate. Lucanthone hydrochloride used for $^{125}$I labeling was 97.5% pure by HPLC mass spectroscopy (Sterling Winthrop Research Institute, R009CJ). $^{125}$I labeled lucanthone was prepared by a modification of the chloramine T method, to be described in detail in a separate publication [Moran JK, Li Y, Deng HF, Labeling and biodistribution of lucanthone (in preparation)]. The product identity was confirmed by thin layer chromatography. $^{99m}$Tc-pertechnetate was obtained from a conventional laboratory supplier. The image acquisitions were performed using a Picker Dyna Camera 4C using Nuclear MAC imaging software running on a Power MAC 8100/80 AV computer. Images were obtained using a pinhole collimator with a collimator to rat distance of 6.5 cm.

Each animal was imaged using $^{99m}$Tc-pertechnetate (3.7 MBq). Pertechnetate was used because it is known not to cross the blood-brain barrier. Therefore, a photopenic area in the image corresponds to the location of the rat brain. As expected, gamma camera scans made 20 min after injection show a photopenic area in the animal's head that corresponds to the location of the brain.

Twenty-four hours following administration of $^{99m}$Tc-pertechnetate, $^{125}$I lucanthone was administered to each test animal. Images were acquired in the left lateral position every 10 min after intravenous administration of 1.1 MBq of $^{125}$I lucanthone. In contrast to the results following administration of $^{99m}$Tc-pertechnetate, the photopenic area is not seen with $^{125}$I lucanthone, showing that this radionuclide readily crossed the blood-brain barrier

Example 3

Organ Analysis of Rat Models

To confirm the findings of Example 2, the biodistribution of $^{125}$I lucanthone was made from determinations of radiolabel contained in various body organs. Male Sprague-Dawley rats (150–180g), purchased from Charles River, received $^{125}$I lucanthone, 0.18 MBq, via tail vein injection. At three time points (20, 45, and 90 min) the animals were sacrificed and tissues were collected (liver, kidney, spleen, muscle, brain, and blood), weighed, and counted. Comparison of muscle and brain showed no significant difference in distribution 20, 45, or 90 min after injection. These data confirm the findings with $^3$H lucanthone in mice, discussed above in Example 1, indicating that lucanthone crossed the blood-brain barrier.

Example 4

Human Clinical Studies

Cancer patients were administered lucanthone hydrochloride in a total dose of 10 mg/Kg per day. The patients were given the drug in three divided doses in order to maintain blood and tissue levels. The total dose was well tolerated. Lucanthone hydrochloride 250 mg tablets for clinical use [GRH/0/1581] were a gift of the Wellcome Foundation. Nausea and other side effects were not observed when patients received 10 mg/Kg.

Quantitative recovery of lucanthone from serum was achieved by an ether extraction method. Serum samples were usually taken 3 hours after the morning dose. Lucanthone was quantitatively recovered from 8 ml of serum by extraction with ether. The upper ether layer was removed and extracted with 0.01N HCl. Lucanthone hydrochloride, now in the aqueous layer, was determined by its UV light spectrum. Comparisons with lucanthone standards at 330 nm and 440 nm verified complete recovery and a linear relationship between the O.D. at 440 nm and the amount of lucanthone assayed, between 2 μg/ml and 6 g/ml. With the dose regimen described above, patients achieved serum levels of ~3 to 4 μg/ml (8–12 μM).

Standard whole brain radiation, 30 Gy with an 8 MeV linear accelerator in ten equal doses over 2 weeks, was given in conjunction with lucanthone at 10 mg/Kg in three doses/day. Patients were assigned to radiation alone or radiation and lucanthone from a table of random numbers. Tumor sizes for each patient were determined before and after therapy independently by two neuroradiologists who had no knowledge of the protocol assignments.

Lucanthone and radiation were well tolerated. Both treatments were omitted on weekends and were stopped after ten treatment days. No abnormal blood or liver chemistries were encountered. No other chemotherapy was given during this time, except steroids, which is standard treatment with patients with brain metastases.

Tumor regression was accelerated in five patients who received lucanthone and 30 Gy compared with three who received 30 Gy alone. The results approach significance using a permutation test at p=0.0536.

What is claimed is:

1. A method of treating a central nervous system cancer sensitive to the combination of radiation and lucanthone in a host comprising:
   administering radiation to the host; and
   administering lucanthone to the host,
   wherein the radiation and lucanthone are administered in amounts effective to cause an arrest or regression of the central nervous system cancer in the host.

2. The method of claim 1, wherein the central nervous system cancer is a metastatic cancer.

3. The method of claim 2, wherein the metastatic cancer comprises adenocarcinomas of a lung, squamous cell carcinomas of a lung, mammary adenocarcinomas, lymphomas, or leukemias.

4. The method of claim 1, wherein the central nervous system cancer is a primary tumor.

5. The method of claim 4, wherein the primary tumor comprises glioblastoma multiforme, astrocytomas, medulloblastomas, acoustic neuromas, or tumors of an anterior and posterior pituitary.

6. The method of claim 1, wherein the radiation is administered in at least about 1 Gray (Gy) fractions at least once every other day to a treatment volume.

7. The method of claim 6, wherein the radiation is administered in at least about 2 Gray (Gy) fractions at least once per day to a treatment volume.

8. The method of claim 1, wherein the radiation is administered in fractions, wherein twenty-three fractions are administered to an initial treatment volume, and another seven treatment fractions are delivered to a boost treatment volume.

9. The method of claim 1, wherein a total of at least about 20 Gy of radiation is administered to the host.

10. The method of claim 9, wherein a total of at least about 30 Gy of radiation is administered to the host.

11. The method of claim 1, wherein a total of at least about 60 Gy of radiation is administered to the host.

12. The method of claim 1, wherein radiation is administered to a whole brain of the host.

13. The method of claim 12, wherein the host is being treated for metastatic cancer.

14. The method of claim 1, wherein the radiation comprises electromagnetic or particulate radiation.

15. The method of claim 14, wherein the electromagnetic radiation comprises x-rays or gamma rays.

16. The method of claim 14, wherein the x-rays comprise supervoltage x-rays.

17. The method of claim 14, wherein the particulate radiation comprises electron beams, protons beams, neutron beams, alpha particles, or negative pi mesons.

18. The method of claim 1, wherein the radiation is provided by targeted delivery or by systemic delivery of targeted radioactive conjugates.

19. The method of claim 1, wherein the lucanthone is administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

20. The method of claim 19, wherein the lucanthone is administered orally.

21. The method of claim 1, wherein the lucanthone is administered in an amount effective to achieve a serum level of at least about 2.0 micrograms/milliliter.

22. The method of claim 1, wherein the lucanthone is administered in an amount effective to achieve a serum level of at least about 3.0 micrograms/milliliter.

23. The method of claim 1, wherein the lucanthone is administered orally at a dosing level of at least about 5 mg/Kg/day.

24. The method of claim 1, wherein the lucanthone is administered orally at a dosing level of at least about 10 mg/Kg/day.

25. The method of claim 1, wherein the lucanthone is administered orally more than once per day.

26. The method of claim 1, wherein the lucanthone is dosed intravenously at 10 mg/kg continuously.

27. The method of claim 1, wherein the lucanthone is dosed intravenously 3.3 mg/kg three times per day for a non-continuous period.

28. The method of claim 1, further comprising:
administering a pharmaceutical agent and an agent that increases permeability through a blood-brain barrier.

29. The method of claim 28, wherein the pharmaceutical agent comprises materials having anti-cancer activity.

30. A method of treating a central nervous system cancer comprising administering an effective amount of radiation to a tumor cell's DNA; and inhibiting excision repair of base damage to the tumor cell's DNA by providing an effective amount of lucanthone to a tumor cell.

* * * * *

UNITED STATES PATENT AND TRADEMARK OFFICE
CERTIFICATE OF CORRECTION

PATENT NO. : 6,391,911 B1
DATED : May 21, 2002
INVENTOR(S) : Bases, R. E.

It is certified that error appears in the above-identified patent and that said Letters Patent is hereby corrected as shown below:

<u>Title page,</u>
Item [56], OTHER PUBLICATIONS,
Regarding the "M.D. Walker" reference, change "Giloma" to -- Glioma --;
Regarding the "Wentland, et al." reference, change "of     N-[[1" to
-- of N-[[1 --;

Signed and Sealed this

Eighth Day of April, 2003

JAMES E. ROGAN
*Director of the United States Patent and Trademark Office*